(12) United States Patent
Fischer et al.

(10) Patent No.: US 6,521,763 B1
(45) Date of Patent: Feb. 18, 2003

(54) METHOD FOR PRODUCING GAMMA-BUTYROLACTONE

(75) Inventors: Rolf Fischer, Heidelberg (DE); Rolf Pinkos, Bad Dürkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/069,771

(22) PCT Filed: Aug. 23, 2000

(86) PCT No.: PCT/EP00/08216

§ 371 (c)(1),
(2), (4) Date: Feb. 28, 2002

(87) PCT Pub. No.: WO01/16126

PCT Pub. Date: Mar. 8, 2001

(30) Foreign Application Priority Data

Sep. 1, 1999 (DE) .......................... 199 41 569

(51) Int. Cl.[7] .............................................. C07D 307/33
(52) U.S. Cl. ...................................................... 549/295
(58) Field of Search .......................................... 549/295

(56) References Cited

U.S. PATENT DOCUMENTS 5,426,195 A    6/1995   Sigg et al. .................. 549/295

FOREIGN PATENT DOCUMENTS

| EP | 584 408 | 3/1994 |
| EP | 628 552 | 12/1994 |
| EP | 848 991 | 6/1998 |
| RO | 91930 | * 6/1997 |
| WO | 92/00973 | 1/1992 |

OTHER PUBLICATIONS

Weissermel et al., *Industrielle Organische Chemie*, 1994, p. 112.

* cited by examiner

*Primary Examiner*—Bernard Dentz
(74) *Attorney, Agent, or Firm*—Keil & Weinkauf

(57) ABSTRACT

In a process for preparing GBL by reaction of 1,4 butanediol over a copper catalyst, use is made of a 1,4 butanediol-containing reaction mixture which comprises further alcohols other than 1,4-butanediol and water.

9 Claims, No Drawings

METHOD FOR PRODUCING GAMMA-BUTYROLACTONE

This application is a 371 of PCT/EP00/08216 filed Aug. 23, 2000.

The present invention relates to a process for preparing gamma-butyrolactone (GBL) by reaction of a 1,4-butanediol-containing reaction mixture over a copper catalyst.

Processes for preparing GBL from 1,4-butanediol have been known for a long time. K. Weissermel, H.-J. Arpe, Industrielle organische Chemie, VCH Verlagsgesellschaft, D 69451 Weinheim, 1994, page 112, describes the dehydrocyclization of 1,4-butanediol over copper catalysts at from 200 to 250° C.

A disadvantage of this process for preparing GBL is that the 1,4-butanediol used has to be purified before use. The purification is usually carried out by means of a complicated multistage distillation in which undesired low- and/or high-boiling constituents, including water, are removed. This water-free pure butanediol is subsequently cyclized to form GBL, with undesirable by-products being formed. For this reason, the cooled GBL again has to be purified by distillation after the reaction. It is thus necessary to carry out two comparable, complicated purification and separation steps.

It is an object of the present invention to provide a process for preparing GBL from 1,4-butanediol in which the butanediol used does not have to be prepurified and the formation of undesirable by-products is avoided.

We have found that this object is achieved by a process for preparing GBL by reaction of 1,4-butanediol over a copper catalyst in which a 1,4-butanediol-containing reaction mixture which comprises further alcohols other than 1,4-butanediol and water is used.

The process of the present invention has the advantage that the 1,4-butanediol-containing reaction mixtures used do not have to be prepurified prior to the reaction to form GBL. 1,4 butanediol can be cyclized to GBL in the presence of further alcohols without appreciable amounts of by-products being formed. This dispenses with the complicated prepurification, so that costs can be saved.

The 1,4-butanediol-containing reaction mixtures used as feed for the reaction can be obtained by known methods.

Thus, for example it is possible to use a 1,4-butanediol-containing reaction mixture which is obtained from acetylene and formaldehyde by the Reppe process and subsequent hydrogenation of the 1,4-butynediol formed, or by acetoxylation or chlorination of butadiene by hydrogenation of 4-hydroxybutyraldehyde and 2,3- or 2,5-dihydrofuran.

The feed used is preferably the hydrogenation product from the hydrogenation of a compound selected from the group consisting of 1,4-butynediol, 4-hydroxybutyraldehyde, 2,3- or 2,5-dihydrofuran, maleic acid, maleic monoesters, maleic diesters and maleic anhydride and/or an intermediate formed in their hydrogenation. Such intermediates are, for example, succinic anhydride, succinic acid or succinic diesters. Particular preference is given to using the hydrogenation product from the hydrogenation of 1,4-butynediol, 4-hydroxybutyraldehyde, maleic acid or maleic diesters as feed in the reaction to form GBL.

The hydrogenation can be carried out in a known manner in the gas phase or the liquid phase. For example, dimethyl maleate can be hydrogenated in the gas phase over a catalyst, e.g. copper chromite, under superatmospheric pressure and at elevated temperature. The hydrogenation product obtained, which is used as feed in the reaction according to the present invention, generally comprises 5–95% by weight of butanediol and 15–95% by weight of alcohol, preferably from 10 to 70% by weight of butanediol and from 5 to 70% by weight of alcohol, particularly preferably from 15 to 60% by weight of butanediol and from 15 to 50% by weight of alcohol. In addition, products such as succinic diesters, water, 4-hydroxybutyric acid and its esters as well as 4 hydroxybutyraldehyde may be present in an amount of up to 30% by weight. The succinic diester content is generally not critical for the process. Furthermore, water may be present in an amount of generally less than 5% by weight, preferably less than 2% by weight, particularly preferably less than 1% by weight, together with small amounts of further compounds. It is also possible for GBL to be present in the hydrogenation product; the GBL content is not critical for the process and may be, for example, from 10 to 30% by weight. If the hydrogenation product from the hydrogenation of 1,4-butynediol, 4-hydroxybutyraldehyde or maleic acid as butanediol source is used, not only water but also generally n-butanol as alcohol component are present. The molar ratio of n-butanol to 1,4-butanediol in these hydrogenation products can be, for example, from 0.5:100 to 5:100.

In place of the total hydrogenation product, it is also possible for only a substream of the hydrogenation product to be fed to the reaction to form GBL. The reaction product of the reaction to form GBL can be fed to the same work-up columns as the substream of the hydrogenation product which has not been reacted further, since both contain similar impurities and by-products. Thus, different apparatuses do not have to be operated for comparable separation tasks.

The reaction mixture in the process of the present invention for preparing GBL generally contains aliphatic alcohols which are preferably monohydric. Aliphatic alcohols having from 1 to 4 carbon atoms, e.g. methanol, ethanol, iso- and n-propanol and n-butanol, are particularly preferably present.

According to the present invention, the 1,4-butanediol-containing reaction mixture is reacted at from 200 to 350° C., preferably from 230 to 330° C., particularly preferably from 230 to 240° C. The reaction is carried out in a pressure range from 0.5 to 10 bar, preferably from 0.8 to 5 bar, particularly preferably from 1 to 3 bar.

Depending on the temperature and pressure conditions selected, the GBL formed and the alcohol and water can go over from the liquid phase to the gaseous phase or remain in the liquid phase. At low reaction pressures, the product stream will leave the reactor in gaseous form. The hydrogen liberated in the reaction can be used as carrier gas for the starting material stream/product stream.

The process of the present invention is carried out using a catalyst which comprises copper either alone or together with at least one metal of transition group VIII of the Period Table, preferably applied to a support.

In principle, all metals of transition group VIII of the Periodic Table can be used in addition to the copper. However, preference is given to using nickel, palladium, cobalt or ruthenium or a mixture of two or more thereof.

The copper content of the catalyst is generally from 1 to 80% by weight, preferably from 3 to 50% by weight and particularly preferably from 5 to 40% by weight, in each case based on the total weight of the catalyst and calculated as metal.

The supported copper catalysts which are preferably used according to the present invention can be produced industrially by applying the copper and, if desired, at least one metal of transition group VIII of the Periodic Table to a support.

The application can be achieved by impregnation of the support in aqueous metal salt solutions, for example aqueous copper solutions, by spraying appropriate metal salt solutions onto the support, by precipitation of the metals and support materials or by other suitable methods.

Suitable copper salts or metal salts of transition group VIII of the Periodic Table are the nitrates, nitrosyl nitrates, halides, carbonates, carboxylates, acetylacetonates, nitrito complexes or ammonia complexes of the corresponding metals, with preference being given to the nitrates, carboxylates and ammonia complexes. When copper salts and metal salts of transition group VIII of the Periodic Table are applied by impregnation, they can be applied to the support either simultaneously or in succession.

The supports which have been coated or impregnated with the metal salt solution are subsequently dried, preferably at from 100 to 150° C., and, if desired, calcined at from 200° C. to 600° C., preferably from 350 to 450° C. In the case of separate impregnation, the catalyst is dried and, if appropriate, calcined after each impregnation step.

The preparation of the catalysts used according to the present invention by precipitation (precipitated catalysts) is carried out by precipitating copper and, if desired, the metals of transition group VIII of the Periodic Table from their salt solutions, e.g. as sparingly soluble hydroxides, hydrated oxides, basic salts or carbonates, subsequently drying the cooled precipitates and then converting these into the corresponding oxides, mixed oxides and/or mixed valence oxides by calcination at generally from 300 to 700° C., in particular from 400 to 600° C. In the preparation of the precipitated catalysts to be used according to the present invention, the precipitation of the catalytically active components can be carried out in the presence of the support material concerned. However, the catalytically active components can also be advantageously precipitated simultaneously with the support material from the appropriate salt solutions.

The precipitated catalysts and the coated and dried and, if desired, calcined catalysts are subsequently activated by treatment in a hydrogen-containing gas stream at from 30 to 600° C., preferably from 150 to 450° C. This activation can advantageously be carried out in situ at the beginning of the reaction or separately before they are used.

As support materials, it is possible to use, in general, the oxides of aluminum and titanium, silicon dioxide, zirconium dioxide, calcium oxide, barium oxide, magnesium oxide and chromium trioxide $Cr_2O_3$). Preferred support materials are the oxides of aluminum, of titanium, silicon dioxide, calcium oxide and magnesium oxide. Of course, it is also possible for mixtures of various support materials to serve as support.

The reaction of the present invention is preferably carried out in the gas phase over fixed-bed catalysts. For example, the reaction of 1,4-butanediol to form GBL can be carried out in the gas phase in a fluidized-bed reactor or a tube reactor. The tube reactor can be carried out in the downflow mode or the upflow mode. The hydrogen liberated in the reaction can be used as carrier gas for the starting material stream/product stream. If the tube reactor is operated in the upflow mode, the high boilers which are formed in the hydrogenation of maleic acid or maleic acid derivatives and are present in the reaction mixture can accumulate in the liquid phase and be bled off as a substream. This can then be discarded or be recirculated to earlier stages of the process, for example the hydrogenation.

The amount of feed per liter of catalyst is generally from 0.05 to 15 kg/h, preferably from 0.1 to 1 kg/h, particularly preferably from 0.2 to 0.8 kg/h.

The conversion of the 1,4-butanediol present in the reaction mixture into GBL is generally from 99 to 100%. Thus, the reaction product after the conversion of 1,4-butanediol into GBL (cyclization product) corresponds essentially to the feed composition, except that the 1,4-butanediol in the feed has been converted into GBL and hydrogen. The cyclization product generally comprises GBL, water and alcohol.

The composition of the cyclization product makes it clear that the reaction of 1,4-butanediol-containing reaction mixtures to form GBL over copper catalysts in the presence of water and further alcohols leads to no appreciable formation of by-products.

The cyclization product can be worked up by distillation using methods known to those skilled in the art.

GBL is a sought-after product and is employed, for example, as an intermediate for preparing pyrrolidones.

The following example illustrates the invention.

EXAMPLES

Example 1

The percentages reported are percentages by weight determined by gas chromatography (method using internal standard).

Preparation of a 1,4-Butanediol-Containing Reaction Mixture (Feed)

The feed was obtained by hydrogenation of a 30% strength aqueous maleic acid solution in the liquid phase at 180–190° C. and 200 bar over a catalyst as described in Example 1 of EP-A 848 991, which comprised platinum, silver, rhenium and iron on activated carbon. The hydrogenation product had the following composition (% by weight): 2.5% of n-butanol, 97.0% of 1,4-butanediol, 0.2% of n-propanol, 0.2% of 2-hydroxytetrahydrofuran plus water and a number of further compounds whose contents were below 0.1%.

Cyclization to GBL

A tube reactor was charged with 100 ml (100 g) of a catalyst consisting of 11% of CuO, 7% of CaO and 82% of $SiO_2$ After activation of the catalyst in a stream of hydrogen, the reactor was heated by means of external heating to bring the internal reactor temperature to 280° C. A continuous hydrogen stream (20 standard 1/h) was then passed through the reactor and the feed (composition as above) was fed in (20 g/h) at 1013 mbar via the bottom of the reactor. After 5 hours, a steady state was established. The gaseous reaction product comprised 2.0% of n-butanol, 97.2% of gamma-butyrolactone, and 0.1% of n-propanol, as well as some further products whose content was less than 0.1% and water.

The GBL yield was over 99%. The catalyst displayed no signs of deactivation even after more than 200 hours.

Part of the reaction product was distilled in a 1 m rotating-ribbon column (20 mbar). The GBL purity achieved was 99.9%.

We claim:

1. A process for preparing gamma-butyrolactone (GBL) by reaction of 1,4-butanediol over a copper catalyst, in which a 1,4-butanediol-containing reaction mixture comprising further alcohols other than 1,4-butanediol and water is used.

2. A process as claimed in claim 1, wherein the reaction mixture is a hydrogenation product from the hydrogenation of a compound selected from the group consisting of 1,4-butynediol, 4-hydroxybutyraldehyde, 2,3- and 2,5 dihydrofuran, maleic acid, maleic monoesters, maleic diesters and maleic anhydride and/or an intermediate formed in the hydrogenation.

3. A process as claimed in claim 1, wherein a monohydric, aliphatic $C_1$–$C_4$-alcohol is used as alcohol.

4. A process as claimed in claim 3, wherein the reaction mixture comprises methanol, ethanol, propanol or n-butanol as alcohol.

5. A process as claimed in claim 1, wherein the reaction is carried out at from 200 to 350° C.

6. A process as claimed in claim 1, wherein the reaction is carried out in a pressure range of from 0.5 to 10 bar.

7. A process as claimed in claim 1, wherein the catalysts comprise copper alone or copper together with a metal of transition group VIII of the Periodic Table of the Elements on a support.

8. A process as claimed in claim 7, wherein the catalysts comprise, as support material, at least one compound selected from the group consisting of the oxides of aluminum and titanium, silicon oxide, zirconium oxide, calcium oxide, barium oxide and chromium trioxide.

9. A process as claimed in claim 1, wherein the reaction is carried out in the gas phase over fixed-bed catalysts.

* * * * *